United States Patent
Shkarlet

[19]

[11] Patent Number: 6,098,466
[45] Date of Patent: Aug. 8, 2000

[54] ULTRASONIC FLOW SENSOR INCORPORATING FULL FLOW ILLUMINATION

[75] Inventor: Yuri Shkarlet, Ithaca, N.Y.

[73] Assignee: Transonic Systems, Inc., Ithaca, N.Y.

[21] Appl. No.: 09/093,981

[22] Filed: Jun. 9, 1998

[51] Int. Cl.⁷ ........................................... G01F 1/66
[52] U.S. Cl. ........................................... 73/861.25
[58] Field of Search ........................ 73/861.27, 861.28, 73/861.29, 861.31, 861.26, 861.25, 861.18, 861.08, 861.05, 866.5, 861

[56] References Cited

U.S. PATENT DOCUMENTS

| | | | |
|---|---|---|---|
| 4,103,551 | 8/1978 | Lynnworth | 73/861.27 |
| 4,227,407 | 10/1980 | Drost | 73/861.28 |
| 4,454,767 | 6/1984 | Shinkai et al. | 73/861.18 |
| 4,754,650 | 7/1988 | Smalling et al. | 73/861.28 |
| 4,850,220 | 7/1989 | Asano et al. | 73/861.28 |
| 5,090,252 | 2/1992 | Tschirner | 73/861.28 |
| 5,179,862 | 1/1993 | Lynnworth | 73/861.28 |
| 5,363,848 | 11/1994 | Spani et al. | 73/861.25 |
| 5,372,047 | 12/1994 | Russwurm et al. | 73/861.29 |
| 5,440,936 | 8/1995 | Spani et al. | 73/861.28 |
| 5,546,812 | 8/1996 | Drenthen | 73/861.29 |
| 5,650,572 | 7/1997 | Vontz | 73/861.28 |

*Primary Examiner*—William Oen
*Assistant Examiner*—Jagdish Patel
*Attorney, Agent, or Firm*—Brown, Pinnisi & Michaels, P.C.

[57] ABSTRACT

An ultrasonic flow sensor probe for measuring fluid (liquid or gas) flow (e.g., blood flow) in vessels or tubes provides decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multidirectional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful in flow measurements on small blood vessels in very small animals. In its simplest form, the present invention includes a two transducer probe with a first reflector surface positioned in the ultrasonic wave path of the first transducer, and a second reflector surface positioned in the wave path of the second transducer. The first reflector surface is positioned to reflect the ultrasonic wave from the first transducer toward the second reflector surface in a direction generally parallel to the flow direction of the vessel or tube. The second reflector surface then reflects the ultrasonic wave through the flow across the wave path from the first transducer and to the second transducer.

45 Claims, 5 Drawing Sheets

ULTRASONIC FLOW SENSOR INCORPORATING FULL FLOW ILLUMINATION

FIELD OF THE INVENTION

The invention pertains to the field of ultrasonic flow sensors for measuring liquid and/or gas flow. More particularly, the invention pertains to measuring blood flow in vessels.

BACKGROUND OF THE INVENTION

Ultrasonic flow sensors have been employed for a number of years for performing intraoperative or extracorporeal blood flow measurements. Intraoperative flow measurements are typically conducted to monitor blood flow in various vessels during vascular, cardiac, transplant, plastic and reconstructive surgery. Extracorporeal blood flow measurements are made externally of the patient during procedures in which the patient's blood is removed for treatment, such as for example, ECMO, hemodialysis, CP bypass and CAVH procedures, by measuring the blood flow as it passes through sterile tubing. These types of flow sensors measure volume flow in the vessels or tubing by employing ultrasonic transit-time principles of operation.

Typically, an ultrasonic flow sensor includes a flow probe that houses two ultrasonic transducers and a fixed acoustic reflector. The transducers are positioned on one side of the vessel or tube under study and the reflector is positioned midway between the two transducers on the opposite side of the vessel or tube. In operation, an electrical excitation is applied to one of the transducers which emits a plane wave of ultrasound. This ultrasonic wave provides full flow illumination of the vessel or tube under study, and first intersects it in the upstream direction. The wave then bounces off of the acoustic reflector, intersects the vessel again, and is finally received by the other transducer which converts it into an electrical signal. From the signal, the flow sensor derives an accurate measure of the "transit time" for the ultrasonic wave to travel from one transducer to the other. This same transmit-receive cycle is then repeated, but with the transmitting and receiving functions of the transducers reversed so that the liquid flow under study is bisected by an ultrasonic wave in the downstream direction. Again, the flow sensor derives an accurate measure of transit time from this transmit-receive sequence.

During the upstream measurement cycle, the ultrasonic wave travels against flow, and this increases the total transit time by a flow dependent amount. Similarly, during the downstream cycle, the ultrasonic wave travels with the flow, thus decreasing the total transit time by the same flow-dependent amount. By subtracting the downstream transit time from the upstream transit time, the ultrasonic flow sensor can therefore determine the fluid volume flow through the vessel or tube.

The foregoing technique works well on straight vessels or tubing carrying a flow without non-axial flow disturbances such as vortexes. Unfortunately, if the vessel or tubing is curved about its longitudinal axis or the flow has vortexes, flow disturbances are created so that the flow volume is no longer uniform across the vessel's cross section.

With a conventional flow probe, if a curvature is applied to a straight vessel or tube, the angles which the two wave paths make with the longitudinal axis of the vessel or tube both either increase or decrease. This results in an inaccurate flow measurement since the change in the time of flight of the ultrasonic wave imparted by the fluid flow is directly proportional to the velocity of the flow and the cotangent of the angle between the flow direction and the ultrasonic wave path. Since the curvature of the vessel or tube either increases or decreases both of these angles, the flow measurements are either too high or too low. As a result, conventional ultrasonic flow sensors are not suitable for use on curved blood vessels or near vessel side branches as are commonly found in humans and other animals, especially small animals.

Figure 6:
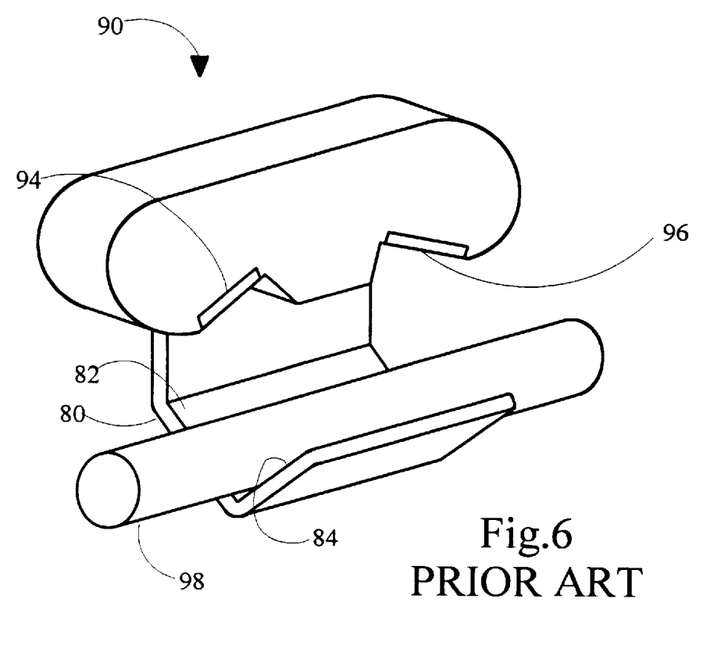
FIG. 6 is a perspective view of a flow sensor probe according to an example of the prior art.
Figure 7:
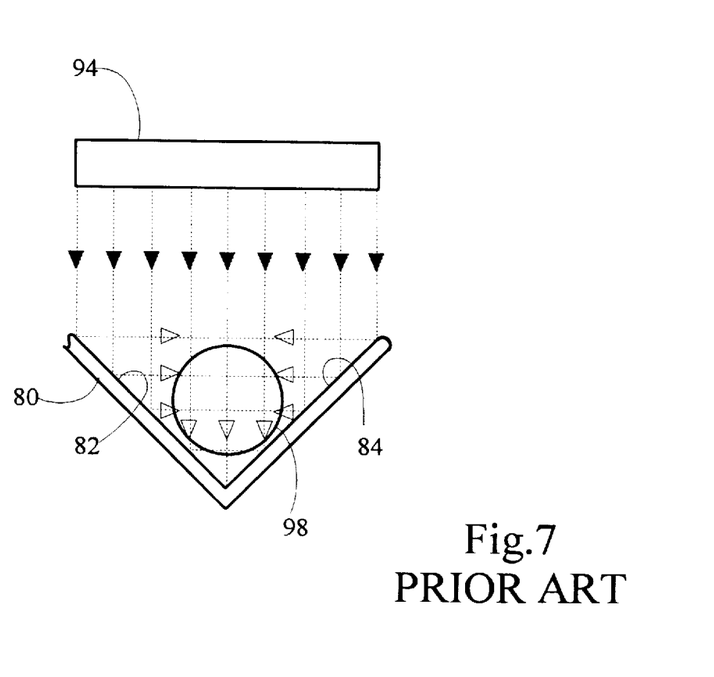
FIG. 7 is a partial side view of the prior art of FIG. 6 where the reflector surfaces are at 90° to each other.

The size of the flow sensor's probe also inherently places limitations on its use. For example, the size of the probe may prevent use of the flow sensor when measurements need to be made on very short blood vessels, such as those which are close to body organs. This is especially of concern in applications involving very small animals, such as mice or rats. The probe size in conventional ultrasonic flow sensors is inherently limited by the fact that the probe must incorporate at least two spaced ultrasonic transducers which must be aimed across the flow path at an angle of less than 90° relative to the flow direction in order to add a flow-dependent component to the transmitted waves. Another factor that also becomes especially important when flow measurements are made on small animals, such as mice or rats, is the flow sensitivity of the probe. With very small diameter blood vessels (e.g., 1 mm or less), the flow rates are also particularly small, requiring that probe flow sensitivity not be sacrificed if accurate measurements are to be made, Referring to FIGS. 6–7, a prior art probe 90 is known which has a reflector 80 with a V-shaped side profile. Reflector 80 includes first and second reflecting surfaces 82 and 84 positioned at a 90° angle with respect to each other. This arrangement of reflecting surfaces 82 and 84 results in an incident ultrasonic wave from a first transducer 94 being split into separate waves as they reflect partly from first reflecting surface 82 and partly from second reflecting surface 84 at the same time. The plane of the ultrasonic wave as it leaves first transducer 94, as shown by the solid arrowheads, thus changes during reflection, as shown by the hollow arrowheads, before being received by a second transducer 96. One disadvantage is that tube 98 must be positioned within the "V" so that the flow information is adequately determined. This limitation in positioning explains why the relative size of the body and reflector of probe 90 is large in comparison to the maximum tube size being measured. An additional disadvantage is that this probe does not provide a sufficient insensitivity to spatial flow non-uniformities, thus limiting the accuracy of the probe.

SUMMARY OF THE INVENTION

Briefly stated, an ultrasonic flow sensor probe for measuring fluid (liquid or gas) flow (e.g., blood flow) in vessels or tubes provides decreased sensitivity to flow distribution non-uniformities and decreased overall size by employing multiple angled reflector surfaces which cause incident ultrasonic waves from one or more ultrasonic transducers to pass through the flow volume multiple times and in multiple directions without changing the planar orientation of the ultrasound waves. The wave paths resulting from the multiple reflections and multidirectional illumination of the flow volume decreases the probe's size and sensitivity to spatial distribution non-uniformities. The multiple angled reflector surfaces also permit the transmitting and receiving ultrasonic transducers to be placed close to one another, thereby reducing the overall probe size and making them particularly useful in flow measurements on small blood vessels in very small animals. In its simplest form, the present invention includes a two transducer probe with a first reflector surface positioned in the ultrasonic wave path of the first transducer, and a second reflector surface positioned in the wave path of the second transducer. The first reflector surface is positioned to reflect the ultrasonic wave from the first transducer toward the second reflector surface in a direction generally parallel to the flow direction of the vessel or tube. The second reflector surface then reflects the ultrasonic wave through the flow across the wave path from the first transducer and to the second transducer.

The present invention employs probe designs having an angled reflector with at least two reflecting surfaces that are arranged so that the ultrasonic wave paths between each probe transducer and the reflector cross each other, thereby permitting the longitudinal spacing between the probe transducers to be reduced substantially. This in turn substantially reduces the size of the flow sensor probe, permitting its use on very short blood vessels as are found small animals such as mice or rats. In addition, the crossed path arrangement cancels the spatial flow distribution effects on measurement results which are caused by a curvature in the vessel or tubing as it passes through the probe.

According to an embodiment of the present invention, an ultrasonic flow sensor probe includes a probe body; at least first and second transducers mounted on the probe body for alternately transmitting and receiving ultrasonic waves passing through a flow volume being measured; and a reflector element mounted on the probe body, such that the reflector element includes at least first and second reflector surfaces, the ultrasonic waves transmitted from the first transducer directly illuminate only the first reflector surface and illuminate the second reflector surface only after being reflected from the first reflector surface, and a plurality of wavefronts from the ultrasonic waves transmitted from the first transducer having a planar orientation retain that same planar orientation when reflected from the first reflector surface to the second reflector surface.

According to an embodiment of the present invention, an ultrasonic flow sensor probe includes a probe body; at least first and second transducers mounted on the probe body for alternately transmitting and receiving ultrasonic waves passing through a flow volume being measured; and a reflector element mounted on the probe body, such that the reflector element includes at least first and second reflector surfaces, and the ultrasonic waves transmitted from the first transducer directly illuminate only the first reflector surface and illuminate the second reflector surface only after being reflected from the first reflector surface.

According to an embodiment of the present invention, an ultrasonic flow sensor probe includes a probe body; at least first and second transducers mounted on the probe body for alternately transmitting and receiving ultrasonic waves passing through a flow volume being measured; and a reflector element mounted on the probe body, such that the reflector element includes at least first and second reflector surfaces, and a plurality of wavefronts from the ultrasonic waves transmitted from the first transducer having a planar orientation retain that same planar orientation when reflected from the first reflector surface to the second reflector surface.

According to an embodiment of the present invention, a method for illuminating a flow volume to be measured includes:
 a) providing a probe body;
 b) alternately transmitting and receiving ultrasonic waves from the probe body through the flow volume being measured; and c) reflecting the ultrasonic waves such that
  i) the ultrasonic waves transmitted from the first transducer directly illuminate only the first reflector surface and illuminate the second reflector surface only after being reflected from the first reflector surface, and
  ii) a plurality of wavefronts from the ultrasonic waves transmitted from the first transducer having a planar orientation retain that same planar orientation when reflected from the first reflector surface to the second reflector surface.

According to an embodiment of the invention, a method for measuring spiral flow components in a flow stream includes:
 a) providing a probe body through which the flow stream travels;
 b) generating at least first and second spiral ultrasonic wave patterns within the flow stream in the probe body such that the first ultrasonic wave pattern travels in a clockwise direction along a flow axis and the second ultrasonic wave pattern travels in a counter-clockwise direction along said flow axis;
 c) detecting the first and second ultrasonic wave patterns;
 d) converting the detected first and second ultrasonic wave patterns to first and second electrical signals; and
 e) determining, from the first and second electrical signals, a quantity and direction of the spiral flow components in the flow stream.

DESCRIPTION OF THE PREFERRED EMBODIMENT

Figure 1A:
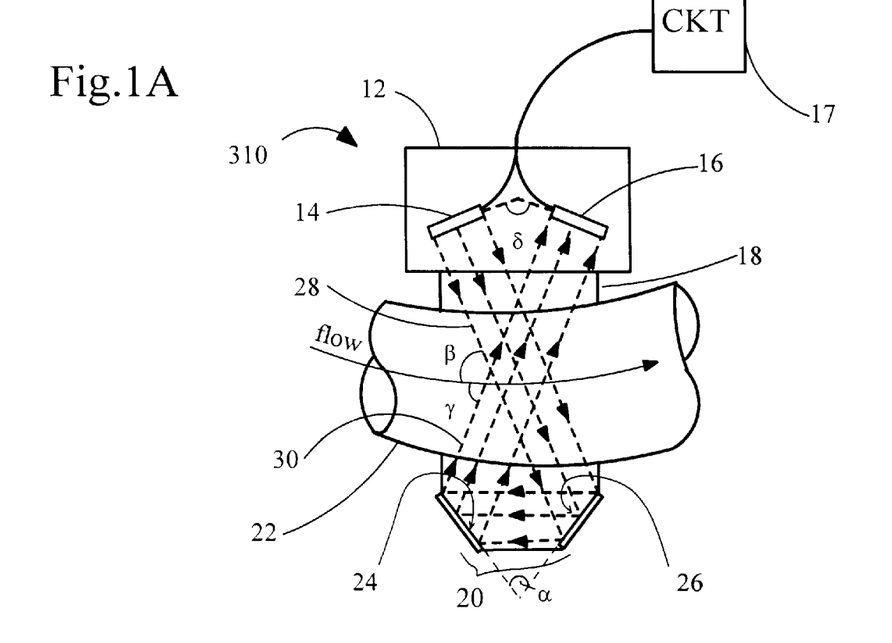
FIG. 1A is a top view of a flow sensor probe design according to an embodiment of the present invention.
Figure 1B:
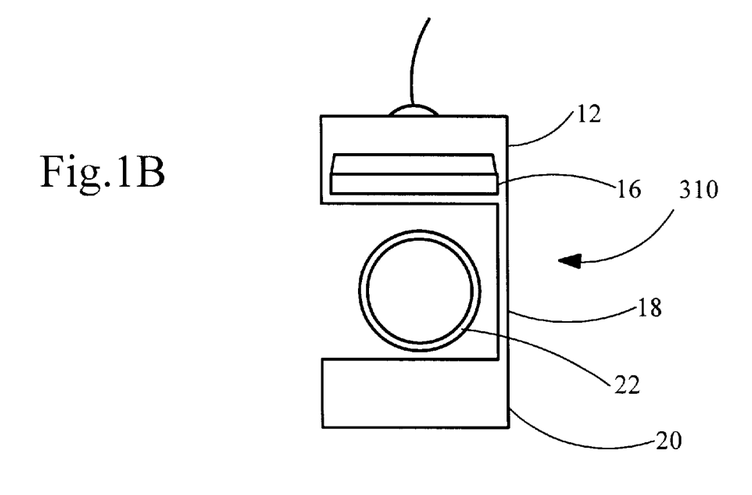
FIG. 1B is a side view of the flow sensor probe design of FIG. 1A.

Referring to FIGS. 1A–1B, an ultrasonic flow sensor probe 310 includes first and second piezoelectric ultrasonic transducers 14 and 16 mounted in a body member 12. Transducers 14 and 16 are of conventional construction, with both being capable of transmitting and receiving ultrasonic waves through conventional electrical excitation and receiving circuitry illustrated generally at 17. First and second transducers 14, 16 alternately transmit and receive ultrasonic waves. First transducer 14 can be in transmit mode while second transducer 16 is in receiver mode, and vice versa. Additionally, first and second transducers 14, 16 can both transmit simultaneously and then simultaneously switch to receive the transmitted signals. In both cases, first and second transducers 14, 16 are alternately transmitting and receiving ultrasonic waves.

An angled reflector 20 is mechanically connected to body member 12 by means of a frame member 18. Frame member 18 optionally includes a transducer support for transducer positioning or a prism. Reflector 20 is held by frame member 18 in a position spaced a sufficient distance from body member 12 so that a vessel or tube 22 containing a fluid flow to be measured can be inserted between body member 12 and reflector 20. An angle $\delta$ measured between the lateral axes of transducers 14 and 16 is preferably between about 40° to 150°.

Angled reflector 20 includes first and second reflector surfaces 26, 24 that are positioned at an angle $\alpha$ relative to one another, where $\alpha$ is $\frac{1}{2}\delta$. Angle $\alpha$ is thus preferably selected to be between 20° and 75°. The spacing between the center points on first and second reflector surfaces 24, 26 is approximately the same as the spacing between the centers of first and second transducers 14, 16. In the present invention, this spacing is twice as small as the spacing in a conventional V-path probe having a similar angle $\delta$.

Transducers 14 and 16 are positioned in body member 12 so that first transducer 14 is aimed substantially at first reflector surface 26 while second transducer 16 is aimed substantially at second reflector surface 24. In this manner, first and second ultrasonic wave paths 28 and 30 are formed which cross each other as they pass through tube 22. The ultrasonic wave travelling along first wave path 28 between first transducer 14 and first reflector surface 26 strikes first reflector surface 26 at less than a 90° angle of incidence, so that the entire wave is reflected across reflector 20 to second reflector surface 24 such that the wave is then reflected along second wave path 30 and received by second transducer 16.

The resulting crossed wave path arrangement is advantageous for two reasons. First, it permits transducers 14 and 16 to be spaced closer together, thereby reducing the size of body member 12 and permitting use of probe 310 on very short blood vessels as are often found on very small animals such as mice or rats. The second advantage of the crossed path arrangement is that it minimizes adverse effects of a non-uniform flow distribution which can occur, for example, from flow vortexes or from tube 22 being curved as illustrated in FIG. 1A. If tube 22 is curved in the direction illustrated in FIG. 1A, an angle $\beta$ that first wave path 28 makes with the flow direction is reduced from what the angle would be if tube 22 is straight, thereby increasing the influence of the flow on the transit time of the wave as it travels along first wave path 28, since the influence is directly proportional to the cotangent of the angle $\beta$.

Similarly, the curvature of tube 22 increases an angle $\gamma$ that second wave path 30 makes with the flow direction from what the angle would be if tube 22 was straight, thereby decreasing the influence of the flow on the transit time of the wave as it travels along second wave path 30. The flow measurement inaccuracies introduced by the increased transit time along first beam path 28 and the decreased transit time along second beam path 30 therefore effectively cancel each other out so that the flow measurement obtained with probe 310 is accurate despite the curvature of tube 22. Accuracy is thus increased over the prior art.

The ultrasonic waves transmitted from first transducer 14 directly illuminate only first reflector surface 26 and illuminate second reflector surface 24 only after being reflected from first reflector surface 26. In similar fashion, the ultrasonic waves transmitted from second transducer 16 directly illuminate only second reflector surface 24 and illuminate first reflector surface 26 only after being reflected from second reflector surface 24.

A result of this arrangement is that the wavefronts from the ultrasonic waves transmitted from first transducer 14 have a planar orientation and retain that same planar orientation when reflected from first reflector surface 26 to second reflector surface 24. The wavefronts from the ultrasonic waves transmitted from second transducer 16 have a planar orientation and retain that same planar orientation when reflected from second reflector surface 24 to first reflector surface 26.

Figures 2A, 2E:
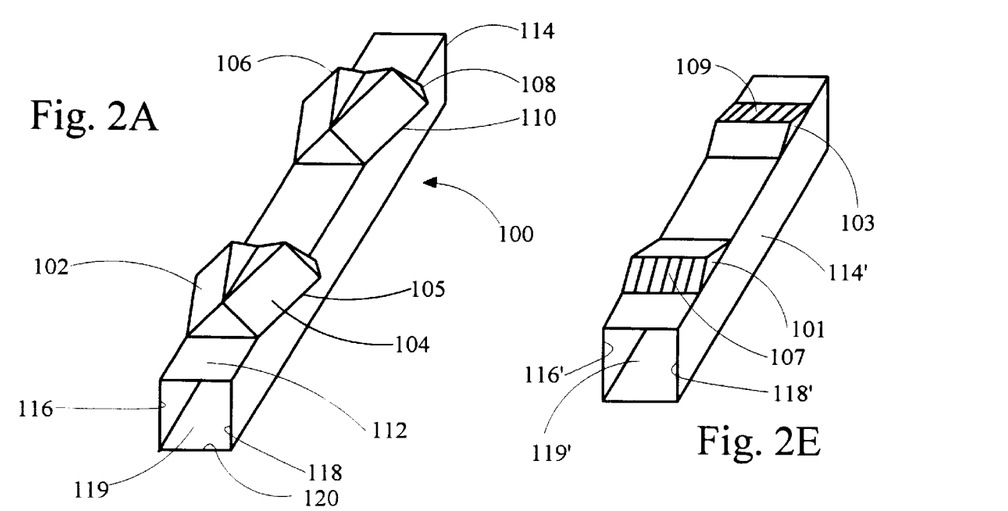
FIG. 2A is a perspective view of a flow sensor probe design according to an embodiment of the present invention.
FIG. 2E is a perspective view of a flow sensor probe design according to an embodiment of the present invention.

Referring to FIG. 2A, a second embodiment of the present invention includes a flow sensor probe 100 in which first and second ultrasonic transducers 102, 104 are mounted on a first transducer support such as first prism structure 105, while third and fourth ultrasonic transducers 106, 108 are mounted on a second transducer support such as second prism structure 110. Each prism structure 105, 110 is disposed in a probe body (not shown) that is mounted on a top surface 112 of a rectangular frame 114. Rectangular frame 114 forms a passage 119 for either the fluid whose flow is to be measured, such as with an in-line sensor, or alternatively, for containing a vessel or tube carrying the fluid, such as with a clamp-on sensor. First and second inside side walls 116, 118 and an inside bottom wall 120 of rectangular frame 114 form three acoustic reflector surfaces. Prism structures 105, 110 are arranged so that the ultrasonic wave paths from each of transducers 102, 104, 106 and 108 preferably form a 45° angle with respect to one of side wall reflector surfaces 116 and 118 and the plane perpendicular to the flow axis of the fluid being measured. Alternatively, the first and second transducer supports can be integral to rectangular frame 114.

Figures 2B, 2C, 2D:
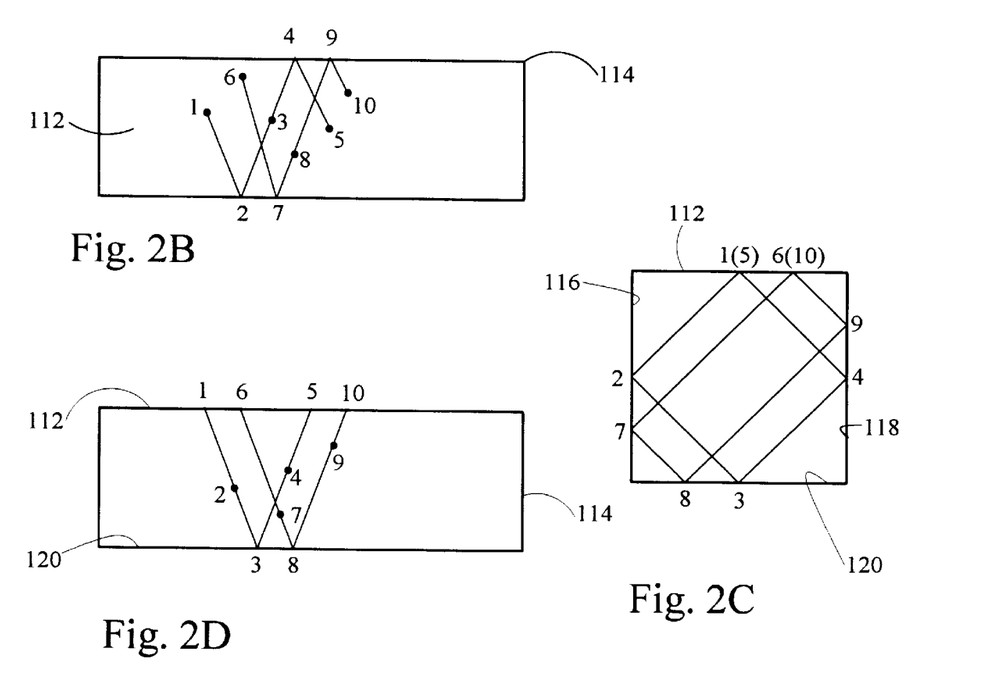
FIG. 2B is a schematic illustration used for explaining the ultrasonic wave paths of the embodiment of FIG. 2A as viewed from the top of FIG. 2A.
FIG. 2C is a schematic illustration used for explaining the ultrasonic wave paths of the embodiment of FIG. 2A as viewed from the front of FIG. 2A.
FIG. 2D is a schematic illustration used for explaining the ultrasonic wave paths of the embodiment of FIG. 2A as viewed from the side of FIG. 2A.

Referring also to FIGS. 2B–2D, reflector surfaces 116, 118, and 120 cause each ultrasonic wave transmitted by any one of transducers 102, 104, 106 and 108 to be reflected three times, thus creating a roughly spiral-type shaped wave path along the flow reflecting at the labeled points 1 to 10 axis before being received by the corresponding receiving transducer.

First and fourth transducers 102 and 108 form a first pair of transducers which can be used independently or together with second and third transducers 104 and 106, which form a second pair. If only one pair of transducers is employed, the spiral-type wave path generated by three reflector surfaces 116, 118 and 120 causes the flow to be illuminated in four different directions, thereby creating a multi-crossing wave pattern which, as in the earlier embodiments, minimizes the effects of non-uniform fluid flow, thus increasing accuracy but still leaving sensitivity to spiral vortexes.

By implementing both pairs of transducers simultaneously, such as with transducers 102 and 104 acting as transmitters and transducers 106 and 108 acting as corresponding receivers, the flow under study is illuminated in eight directions, thereby forming two spiral-type wave paths along the flow axis. One spiral-type wave path, provided by first pair of transducers 102 and 108, is clockwise, while the second spiral-type wave path, provided by second pair of transducers 104 and 106, is counterclockwise.

This arrangement better minimizes the effects of non-uniform fluid flow and the cancels the effects of spiral-type flow components such as vortexes. Accuracy is thus increased over the prior art. By determining the difference of the two signals generated and received by each pair of transducers, an estimation of the quantity of spiral-type flow components is made, whereby the character of this difference gives information on the spiral-type component direction.

As with the first embodiment of FIGS. 1A–1B, the ultrasonic waves transmitted from the transducers directly illuminate only one reflector surface. Each succeeding reflector surface is illuminated in turn. This arrangement results in the planar wavefronts from the transmitted ultrasonic waves to retain their planar orientation during reflection.

Referring to FIG. 2E, two simple prism structures 101, 103 are mounted on a rectangular frame 114'. Transducer arrays 107 and 109 each contain a plurality of transducers that send ultrasonic waves angled towards both reflecting surfaces 116', 118' at an angle with respect to a longitudinal axis of a passage 119'. A bi-directional spiral-type wave path is thus achieved which is similar to the two-pair case of the embodiment of FIG. 2A. High accuracy is thus achieved with a simpler prism geometry.

Figures 3A, 3B:
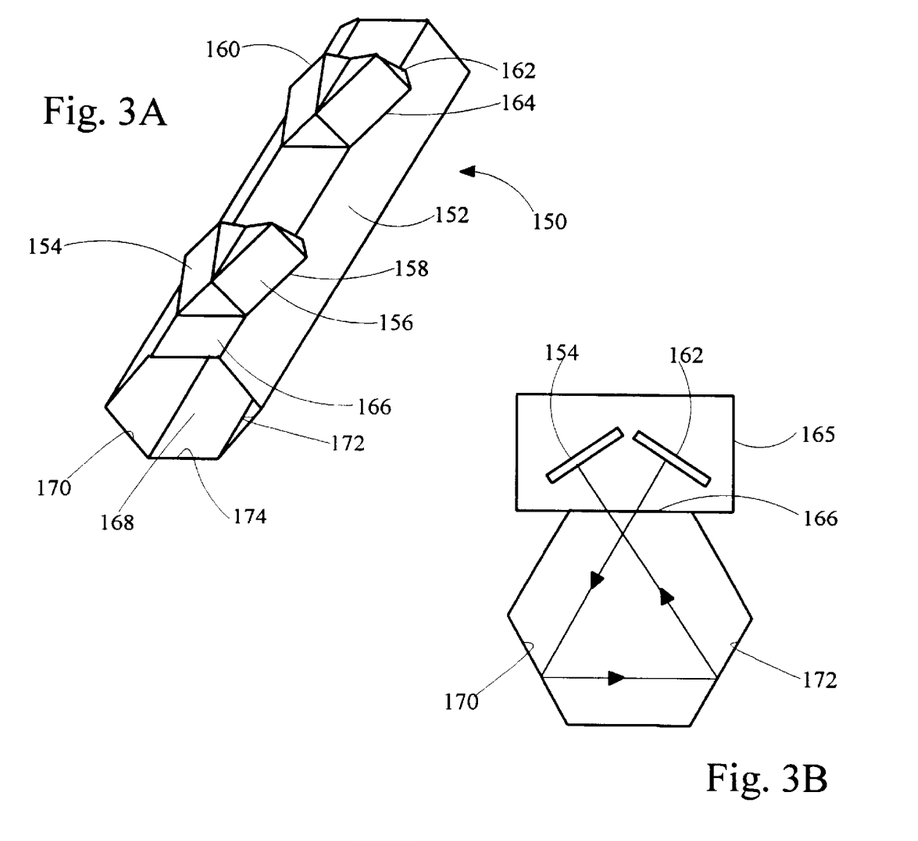
FIG. 3A is a perspective view of a flow sensor probe design according to an embodiment of the present invention.
FIG. 3B is a partial sectional front view of the embodiment of FIG. 3A.

Referring to FIGS. 3A–3B, a third embodiment of the present invention includes ultrasonic sensor probe 150. Probe 150 differs from probe 100 of FIG. 2A in that a hexagonal channel member 152 is used in place of rectangular frame 114 for forming a passage 168 for either the fluid whose flow is to be measured, such as in an in-line sensor, or alternatively, for a vessel or tube carrying the fluid being measured, such as with a clamp-on sensor. Probe 150 includes first and second ultrasonic transducers 154, 156 mounted on a first prism structure 158, with third and fourth ultrasonic transducers 160, 162 mounted on a second prism structure 164. Optionally, only transducers 154 and 162 are provided.

First and second prism structures 158 and 164 are disposed in a probe body (not shown) that is mounted on a top surface 166 of hexagonal channel member 152. Hexagonal channel member 152 includes first and second lower inner side walls 170 and 172 that constitute two acoustic reflector surfaces which are positioned at a 120° angle with respect to a bottom inner surface 174 of channel member 152. Each of ultrasonic transducers 154, 156, 160 and 162 is mounted on its corresponding prism structure 158, 164 in such a way that the ultrasonic wave propagation direction from any of the transducers preferably forms a 60° angle with respect to one or the other of reflecting surfaces 170 and 172 and to a plane perpendicular to the flow axis. As with the second embodiment, transducer supports that are integral or one-piece with hexagonal channel member 152 can optionally be used instead of first and second prism structures 158, 164.

Reflector surfaces 170 and 172 cause each incident ultrasonic wave to be reflected twice, thus making a spiral-type wave path along the flow axis before the wave is received by the corresponding receiving transducer. If only one pair of the transducers is provided or employed (e.g., transducers 154, 162 or 156, 160), the flow is illuminated in three different directions, thereby creating a multi-crossing wave pattern which minimizes the effects of non-uniform fluid flow but still leaves the effects of spiral-type vortexes. Using both pairs of transducers 154, 162 and 156, 160 simultaneously to provide flow illumination in six directions cancels the effects of spiral-type flow components and results in high minimization of the effects of non-uniform fluid flow, thereby increasing accuracy. An estimation of the quantity of spiral type flow components can be made and the character of this difference can provide information on the spiral type component direction.

Figure 3C:
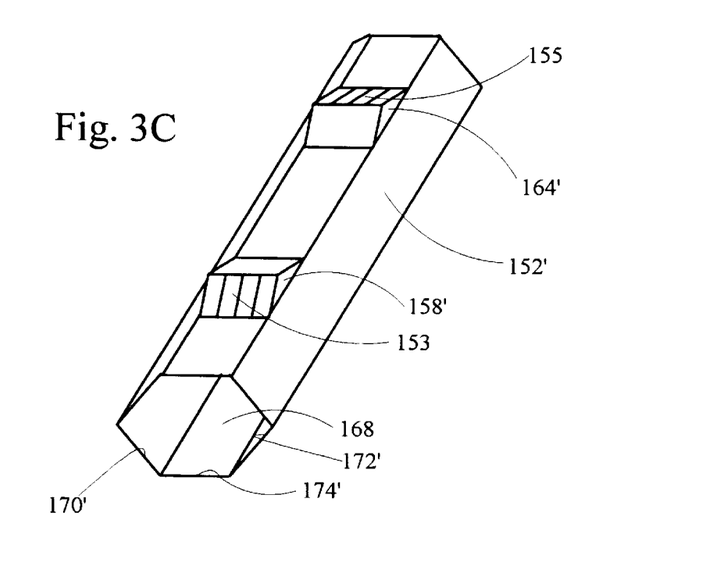
FIG. 3C is a perspective view of a flow sensor probe design according to an embodiment of the present invention.

Referring to FIG. 3C, two simple prism structures 158', 164' are mounted on a hexagonal channel member 152'. Transducer arrays 153 and 155 each contain a plurality of transducers that send ultrasonic waves angled towards reflecting surfaces 170', 172' at an angle with respect to a longitudinal axis of a passage 168'. A bi-directional spiral-type wave path and simultaneous flow illumination in six directions is thus achieved, resulting in increased accuracy with a simple prism geometry.

As with the first and second embodiments, the ultrasonic waves transmitted from the transducers directly illuminate only one reflector surface. Each succeeding reflector surface is illuminated in turn. This arrangement results in the planar wavefronts from the transmitted ultrasonic waves to retain their planar orientation during reflection.

The main advantage of the third embodiment is that hexagonal shaped channel 152 is much closer to the cross-sectional shape of round tubing, and its larger 120° angles decrease the occurrence of particle deposits at the inside corners of channel member 152 that tend to occur during measurements of high viscosity liquids or liquids with components which cause deposits to form. This advantage is also important for medical applications because the hexagonal shape prevents blood clotting at the inside corners of hexagonal channel member 152. In addition, the larger angles of the hexagonal channel provide a smoother, and therefore safer, external shape which is very important in medical applications.

Figures 4A, 4B, 5:
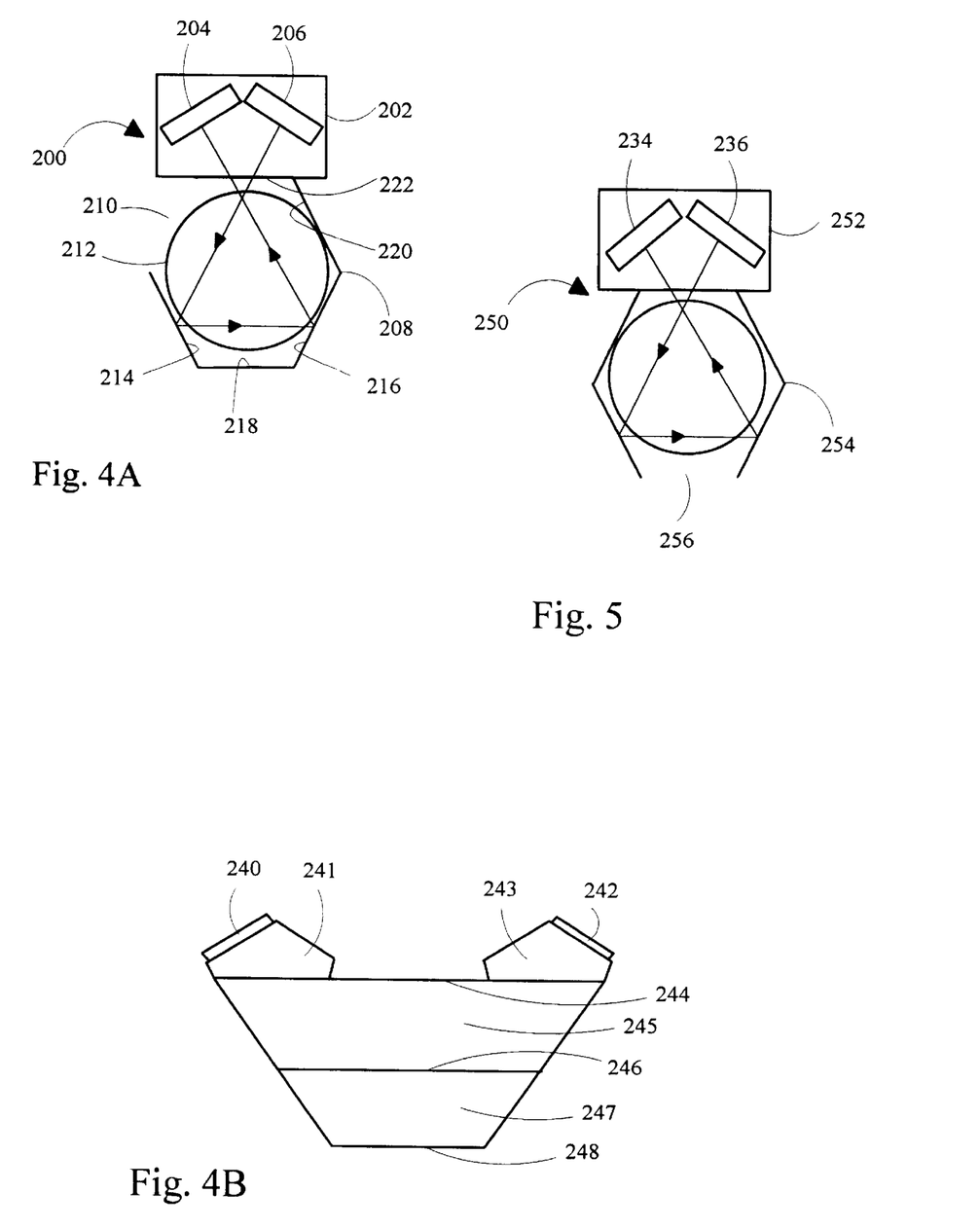
FIG. 4A is a partial sectional front view of a variation of the embodiment of FIG. 3A.
FIG. 4B is a side view of the embodiment of FIG. 4A.
FIG. 5 is a partial sectional front view of a variation of the embodiment of FIG. 3A.

Referring to FIG. 4A, a variation of the third embodiment of the present invention includes an ultrasonic flow sensor probe 200 with a body member 202 in which first and second ultrasonic transducers 204 and 206 are mounted in the same way as in probe 150 of the third embodiment. While only one pair of transducers is illustrated, two pairs of transducers can be optionally employed as in the previous embodiments. First transducer 204 corresponds to transducer 154 of FIG. 3A while second transducer 206 corresponds to transducer 162 of FIG. 3A. The phrase "pairs of transducers" thus refers to transmitting and receiving pairs and not to the two transducers on the same prism or transducer support.

Probe 200 differs from probe 150 in that it includes a five sided frame member 208 that forms an opening 210 for reception of a vessel or tube 212. First and second inside lower side walls 214 and 216 of frame member 208 form acoustic reflector surfaces which are positioned and function the same as acoustic reflector surfaces 170 and 172 of probe 150. Nonreflecting surfaces of frame member 208, including a bottom side 218, an upper side wall 220, and a top side 222, need not be flat, but can be optionally curved in accordance with the curvature of tube 212.

Referring to FIG. 4B, another variation of the third embodiment is shown in a side view where a transducer 240 on a prism 241 corresponds to transducer 154 on prism 158 of FIG. 3A and a transducer 242 on a prism 243 corresponds to transducer 162 on prism 164 of FIG. 3A. Transducers 240 and 242 are thus "paired transducers" as that phrase is used in this disclosure. An edge 244 separates a top side (not shown) from a first side 245. An edge 246 separates first side 245 from a second side 247. An edge 248 separates second side 247 from a bottom side (not shown). The bottom side (not shown) corresponds to bottom side 218 in the embodiment shown in FIG. 4A and to opening 256 in the embodiment shown in FIG. 5.

The inside reflecting surface (not shown) of second side 247 corresponds to second inside lower side wall 216 of FIG. 4A. Sides 245 and 247 are preferably formed trapezoidally as shown, as is the side (not shown) that corresponds to first inside lower side wall 214 of FIG. 4A. The trapezoidal shape of the sides results in a decreased size of a lower part of the probe along the vessel being measured, thus providing for a less traumatic insertion of the probe into a person or animal.

Referring to FIG. 5, another variation of the third embodiment of the present invention includes a probe 250 which differs from probe 200 of the embodiment shown in FIG. 4A only in that a body member 252 is mounted on a five sided frame member 254 in such a way that an opening 256 is located at the bottom of frame member 254 instead at one side. This design is particularly advantageous in medical applications because it provides easier access to hard to reach vessels so that measurements may be obtained in a way that is much less traumatic for adjacent tissues. A modification of this variation includes trapezoidally shaped sides as shown in FIG. 4B.

The third embodiment of FIGS. 3A–3C and its variations as shown in FIGS. 4A–4B and FIG. 5 all share the same ultrasonic wave patterns. The third embodiment can optionally be modified to include trapezoidally shaped sides. The variations of FIGS. 4A–4B and FIG. 5 advantageously permit convenient insertion of the vessel or tube whose flow is being measured within the frame member.

The present invention provides a number of ultrasonic flow sensor probe designs, all of which result in decreased sensitivity to spatial distribution of flow non-uniformities, thus increasing measurement accuracy. In addition, these designs result in probes of decreased size, thereby making all of the probes particularly useful in applications requiring fluid flow measurement in very small vessels or tubes, on very short blood vessels, or on vessels that are difficult to reach. All of the probe designs incorporate multiple angled reflector surfaces which create multi-crossed ultrasonic wave paths and multi-directional flow illumination for decreased sensitivity to spatial distribution non-uniformities and decreased probe size.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. An ultrasonic flow sensor probe comprising:
   a) a probe body;
   b) at least first and second transducers mounted on said probe body for alternately transmitting and receiving ultrasonic waves passing through a flow volume being measured, wherein said transducers are positioned such that a full cross-sectional area of said flow volume is evenly illuminated; and
   c) a reflector element on said probe body, such that
      i) said reflector element includes at least first and second reflector surfaces;
      ii) said ultrasonic waves transmitted from said first transducer directly illuminate only said first reflector surface and illuminate said second reflector surface only after being reflected from said first reflector surface; and
      iii) a plurality of wavefronts from said ultrasonic waves transmitted from said first transducer having a planar orientation retain that same planar orientation when reflected from said first reflector surface to said second reflector surface.

2. An ultrasonic flow sensor probe according to claim 1, wherein said at least first and second transducers are contained within first and second transducer arrays, respectively.

3. An ultrasonic flow sensor probe according to claim 1, wherein:
   said at least first and second transducers are mounted on first and second prisms; and
   said first and second prisms are mounted on said probe body.

4. An ultrasonic flow sensor probe according to claim 3, wherein said probe body is a rectangular channel.

5. An ultrasonic flow sensor probe according to claim 3, wherein said probe body is a hexagonal channel.

6. An ultrasonic flow sensor probe according to claim 1, further comprising:
   d) third and fourth transducers mounted in said probe body for alternately transmitting and receiving ultrasonic waves passing through said flow volume being measured; and
   e) a third reflector surface.

7. An ultrasonic flow sensor probe according to claim 6, wherein:
   i) said first and third transducers are mounted on a first prism;
   ii) said second and fourth transducers are mounted on a second prism; and
   iii) said first and second prisms are mounted on said probe body.

8. An ultrasonic flow sensor probe according to claim 6, wherein said reflector element includes a rectangular frame member with said first, second, and third reflector surfaces comprising three sides of said rectangular frame member.

9. An ultrasonic flow sensor probe according to claim 1, wherein said reflector element includes a hexagonal frame member with said first and second reflector surfaces comprising two sides of said hexagonal frame member.

10. An ultrasonic flow sensor probe according to claim 9, wherein said hexagonal frame member includes an opening in a non-reflecting surface.

11. The ultrasonic flow sensor probe of claim 1, comprising rectangular transducers that generate plane-wave rectangular beams.

12. An ultrasonic flow sensor probe comprising:
    a) a probe body;
    b) at least first and second transducers mounted on said probe body for alternately transmitting and receiving ultrasonic waves passing through a flow volume being measured, wherein said transducers are positioned such that a full cross-sectional area of said flow volume is evenly illuminated; and
    c) a reflector element on said probe body, such that
       i) said reflector element includes at least first and second reflector surfaces; and
       ii) said ultrasonic waves transmitted from said first transducer directly illuminate only said first reflector surface and illuminate said second reflector surface only after being reflected from said first reflector surface.

13. An ultrasonic flow sensor probe according to claim 12, wherein said at least first and second transducers are contained within first and second transducer arrays, respectively.

14. An ultrasonic flow sensor probe according to claim 12, wherein:
   said at least first and second transducers are mounted on first and second prisms; and
   said first and second prisms are mounted on said probe body.

15. An ultrasonic flow sensor probe according to claim 14, wherein said probe body is a rectangular channel.

16. An ultrasonic flow sensor probe according to claim 14, wherein said probe body is a hexagonal channel.

17. An ultrasonic flow sensor probe according to claim 12, further comprising:
   d) third and fourth transducers mounted in said probe body for alternately transmitting and receiving ultrasonic waves passing through said flow volume being measured; and
   e) a third reflector surface.

18. An ultrasonic flow sensor probe according to claim 17, wherein:
   i) said first and third transducers are mounted on a first prism;
   ii) said second and fourth transducers are mounted on a second prism; and
   iii) said first and second prisms are mounted on said probe body.

19. An ultrasonic flow sensor probe according to claim 17, wherein said reflector element includes a rectangular frame member with said first, second, and third reflector surfaces comprising three sides of said rectangular frame member.

20. An ultrasonic flow sensor probe according to claim 12, wherein said reflector element includes a hexagonal frame member with said first and second reflector surfaces comprising two sides of said hexagonal frame member.

21. An ultrasonic flow sensor probe according to claim 20, wherein said hexagonal frame member includes an opening in a non-reflecting surface.

22. The ultrasonic flow sensor probe of claim 12, comprising rectangular transducers that generate plane-wave rectangular beams.

23. An ultrasonic flow sensor probe comprising:
   a) a probe body;
   b) at least first and second transducers mounted on said probe body for alternately transmitting and receiving ultrasonic waves passing through a flow volume being measured, wherein said transducers are positioned such that a full cross-sectional area of said flow volume is evenly illuminated; and
   c) a reflector element on said probe body, such that
      i) said reflector element includes at least first and second reflector surfaces; and
      ii) a plurality of wavefronts from said ultrasonic waves transmitted from said first transducer having a planar orientation retain that same planar orientation when reflected from said first reflector surface to said second reflector surface.

24. An ultrasonic flow sensor probe according to claim 23, wherein said at least first and second transducers are contained within first and second transducer arrays, respectively.

25. An ultrasonic flow sensor probe according to claim 23, wherein:
   said at least first and second transducers are mounted on first and second prisms; and
   said first and second prisms are mounted on said probe body.

26. An ultrasonic flow sensor probe according to claim 25, wherein said probe body is a rectangular channel.

27. An ultrasonic flow sensor probe according to claim 25, wherein said probe body is a hexagonal channel.

28. An ultrasonic flow sensor probe according to claim 23, further comprising:
   d) third and fourth transducers mounted in said probe body for alternately transmitting and receiving ultrasonic waves passing through said flow volume being measured; and
   e) a third reflector surface.

29. An ultrasonic flow sensor probe according to claim 28, wherein:
   i) said first and third transducers are mounted on a first prism;
   ii) said second and fourth transducers are mounted on a second prism; and
   iii) said first and second prisms are mounted on said probe body.

30. An ultrasonic flow sensor probe according to claim 28, wherein said reflector element includes a rectangular frame member with said first, second, and third reflector surfaces comprising three sides of said rectangular frame member.

31. An ultrasonic flow sensor probe according to claim 28, wherein said reflector element includes a hexagonal frame member with said first and second reflector surfaces comprising two sides of said hexagonal frame member.

32. An ultrasonic flow sensor probe according to claim 31, wherein said hexagonal frame member includes an opening in a non-reflecting surface.

33. The ultrasonic flow sensor probe of claim 23, comprising rectangular transducers that generate plane-wave rectangular beams.

34. A method for illuminating a flow volume to be measured, comprising:
   a) providing a probe body with at least first and second transducers mounted on said probe body, wherein said transducers are positioned such that a full cross-sectional area of said flow volume is evenly illuminated;
   b) alternately transmitting and receiving ultrasonic waves from said probe body through said flow volume being measured; and
   c) reflecting said ultrasonic waves such that
      i) said ultrasonic waves transmitted from said first transducer directly illuminate only a first reflector surface and illuminate a second reflector surface only after being reflected from said first reflector surface, and
      ii) a plurality of wavefronts from said ultrasonic waves transmitted from said first transducer having a planar orientation retain that same planar orientation when reflected from said first reflector surface to said second reflector surface.

35. The method of claim 34, wherein said transducers are rectangular and generate plane-wave rectangular beams.

36. The method of claim 34, wherein at least one passive reflector is used to cause at least one of said ultrasonic wavefronts to intersect itself in a central region of a flow conduit.

37. The method of claim 34, wherein said ultrasound probe body is loosely applied around a vessel conduit of arbitrary shape and diameter.

38. A method for measuring spiral flow components in a flow stream, comprising:
   a) providing a probe body through which said flow stream travels;
   b) providing transducers generating at least first and second spiral ultrasonic wave patterns within said flow stream in said probe body such that said first ultrasonic wave pattern travels in a clockwise direction along a flow axis and said second ultrasonic wave pattern travels in a counter-clockwise direction along said flow axis, wherein said transducers are positioned such that a full cross-sectional area of said flow volume is evenly illuminated;
   c) detecting said first and second ultrasonic wave patterns;
   d) converting said detected first and second ultrasonic wave patterns to first and second electrical signals; and
   e) determining, from said first and second electrical signals, a quantity and direction of said spiral flow components in said flow stream.

39. A method according to claim 38, further comprising determining a flow of said flow stream from said first and second electrical signals.

40. The method of claim 34, wherein said transducers are rectangular and generate plane-wave rectangular beams.

41. An ultrasonic flow sensor probe comprising:
   a) a probe body comprising a hexagonal channel;
   b) at least first and second transducers mounted on said probe body for alternately transmitting and receiving ultrasonic waves passing through a flow volume being measured, wherein said transducers are positioned such that a full cross-sectional area of said flow volume is evenly illuminated; and
   c) a reflector element on said probe body, such that
      i) said reflector element includes at least first and second reflector surfaces; and
      ii) a plurality of wavefronts from said ultrasonic waves transmitted from said first transducer having a planar orientation retain that same planar orientation when reflected from said first reflector surface to said second reflector surface.

42. The ultrasonic flow sensor probe of claim 41, comprising rectangular transducers that generate plane-wave rectangular beams.

43. The ultrasonic flow sensor probe of claim 41, wherein at least one wall of said hexagonal channel is modified to allow entry of a sample vessel into an ultrasound window.

44. An ultrasonic flow sensor probe comprising:
   a) a probe body; and
   b) at least first and second transducers mounted on said probe body for generating at least first and second spiral ultrasonic wave patterns within a flow volume being measured in said probe body, such that said first ultrasonic wave pattern travels in a clockwise direction along a flow axis and said second ultrasonic wave pattern travels in a counter-clockwise direction along said flow axis and wherein said transducers are positioned such that a full cross-sectional area of said flow volume is evenly illuminated.

45. The ultrasonic flow sensor probe of claim 44, comprising rectangular transducers that generate plane-wave rectangular beams.

* * * * *